United States Patent
Farin et al.

(10) Patent No.: US 7,354,435 B2
(45) Date of Patent: Apr. 8, 2008

(54) ELECTROSURGICAL INSTRUMENT

(75) Inventors: Günter Farin, Tübingen (DE); Daniel Schäller, Tübingen (DE); Matthias Voigtländer, Gomaringen (DE)

(73) Assignee: Erbe Elektromedizin GmbH, Tubingen (DE)

( * ) Notice: Subject to any disclaimer, the term of this patent is extended or adjusted under 35 U.S.C. 154(b) by 392 days.

(21) Appl. No.: 10/478,367

(22) PCT Filed: Jun. 20, 2002

(86) PCT No.: PCT/EP02/06857

§ 371 (c)(1),
(2), (4) Date: Nov. 21, 2003

(87) PCT Pub. No.: WO03/000149

PCT Pub. Date: Jan. 3, 2003

(65) Prior Publication Data

US 2004/0138658 A1     Jul. 15, 2004

(30) Foreign Application Priority Data

Jun. 22, 2001 (DE) .............................. 101 29 699

(51) Int. Cl.
*A61B 18/14* (2006.01)

(52) U.S. Cl. ........................................ 606/32; 606/49

(58) Field of Classification Search .................. 606/41, 606/32, 49; 607/98; 604/95.01, 95
See application file for complete search history.

(56) References Cited

U.S. PATENT DOCUMENTS

| 4,580,551 | A | * | 4/1986 | Siegmund et al. ........... 600/139 |
| 5,441,483 | A | * | 8/1995 | Avitall ...................... 604/95.05 |
| 5,697,927 | A | * | 12/1997 | Imran et al. .................. 606/41 |
| 5,720,745 | A | * | 2/1998 | Farin et al. ................... 606/49 |
| 6,039,736 | A | | 3/2000 | Platt, Jr. ....................... 606/49 |
| 6,197,026 | B1 | * | 3/2001 | Farin et al. ................... 606/49 |
| 6,852,112 | B2 | * | 2/2005 | Platt ............................. 606/49 |
| 2003/0105458 | A1 | | 6/2003 | Platt | |

FOREIGN PATENT DOCUMENTS

| DE | 297 24 247 U1 | 9/2000 |
| EP | 1 090 597 A1 | 4/2001 |
| JP | 2001-145633 | 5/2001 |

* cited by examiner

Primary Examiner—Lee S. Cohen
(74) Attorney, Agent, or Firm—Dickstein Shapiro LLP

(57) ABSTRACT

Electrosurgical instrument for the coagulation of biological tissue, wherein from a gas source a noble gas is sent through a tubular probe to at least one outflow opening in a distal end region of the probe, with an electrode device disposed in the distal end region of the probe, which can be connected to an HF source in order to supply a coagulation current, and wherein the at least one outflow opening has a slit-like structure, such that at least two outflow openings are provided, disposed opposite one another with their long axes oriented perpendicular to or at an angle to, but not parallel to a long axis of the probe, and that the probe is flexibly constructed at least in the region of the outflow openings, in such a way that when the probe is bent in the region of the outflow openings, their cross sections are enlarged or reduced.

19 Claims, 2 Drawing Sheets

ELECTROSURGICAL INSTRUMENT

RELATED U.S. APPLICATIONS

This is the U.S. national phase of International Application No. PCT/EP02/06857 filed Jun. 20, 2002 the entire disclosure of which is incorporated herein by reference.

FIELD OF THE INVENTION

The invention relates to an electrosurgical instrument for the coagulation of biological tissues.

BACKGROUND OF THE INVENTION

Plasma surgery is a form of monopolar high-frequency surgery (HF surgery) in which a high-frequency electrical current (HF current) produced by a high-frequency generator (HF generator) is passed through an ionized noble gas (plasma), for instance argon (argon plasma), from an electrical pole within a suitably designed surgical instrument to the tissue that is to be treated by current application, and is conducted back from that site to the HF generator through a so-called neutral electrode in contact with the patient (G. Farin et al.: Technology of Argon Plasma Coagulation with Particular Regard to Endoscopic Applications; Endoscopic Surgery and Allied Technologies, No. 1, Vol. 2, February 1994, 71-77). By this means heat is introduced into the tissue, both endogenously by the HF current and exogenously because the plasma is at a higher temperature than the tissue, as a result of which the tissue temperature rises. In dependence on the temperature various thermal effects are induced in the tissue, which can be exploited by surgeons for a variety of therapeutic purposes, such as stopping bleeding (hemostasis) and/or thermal devitalization or destruction of pathological tissue (K. E. Grund et al.: Argon Plasma Coagulation in Flexible Endoscopy, Endoscopic Surgery and Allied Technologies, No. 1, Vol. 2, February 1994, 42-46).

An important physical prerequisite for plasma surgery is that a noble gas, for example the above-mentioned argon or helium, must be present between an electrical pole, formed by an electrode within the instrument, and the tissue to be treated. The reason is that noble gases can be ionized with relatively low electrical field strength, in comparison to oxygen and/or nitrogen or to air, and do not enter into chemical reactions with the tissue. Potential consequences such as carbonization or even vaporization of the tissue are thus avoided.

Within the last five years the spectrum of indications for plasma surgery, in particular when combined with flexible endoscopy, has become very broad (K. E. Grund: DMW), placing a range of new demands on the associated technology and the necessary instruments, HF generators and gas sources.

The German patent DE 198 20 240 A1 discloses a probe according to the precharacterizing clause of claim 1 that enables large-area lesions to be treated better than previously. However, especially when the plasma surgery must be employed in confined body cavities or hollow organs, the use of instruments according to DE 198 20 240 A1 can cause problems. First, with those that have only one opening on the side, it may be difficult to direct this opening toward the target tissue, i.e. the lesion for which coagulation is intended. On the other hand, when there are several openings distributed around the circumference of an instrument as specified in DE 198 20 240 A1, problems may result from unintended coagulation of parts of the tissue other than the target site. The latter can occur when the distance separating the instrument from tissues that should not or must not be coagulated is smaller than that to the target tissue.

BRIEF SUMMARY OF THE INVENTION

The object of the present invention is to develop a probe of the kind mentioned above in such a way as to enable improved manipulation, in particular with respect to controlling the spatial positioning of the plasma.

According to the present invention there is provided an electrosurgical instrument for the coagulation of biological tissue comprising a tubular probe through which a noble gas from a gas source can be passed to at least two outflow openings defined in a distal end region of the probe, the at least two outflow openings each having a slit-like structure; and an electrode device disposed in the distal end region of the probe, which device can be connected to an HF source in order to supply a coagulation current; the at least two outflow openings being provided, disposed opposite one another with their long axes oriented perpendicular to or at an angle to, but not parallel to a long axis of the probe, and the probe being flexibly constructed at least in the region of the outflow openings, in such a way that when the probe is bent in the region of the outflow openings, their cross sections are enlarged or reduced.

A substantial aim of the invention lies in that fact that because bending of the instrument in the region of the outflow openings is possible and easy for the operator to accomplish, the current of gas can be controlled, and this in turn has a considerable influence on the orientation of the plasma and hence of the arc.

Furthermore, a more uniform flow of argon all around the instrument, even when the latter is not bent, is produced by providing several outflow openings offset from one another by specified angles with respect to the circumference of the instrument. As a result, the user can apply the treatment to specifically targeted lesions more simply than was previously possible. This goal of making the argon flow uniform all around the instrument is preferably achieved by disposing the slit-like outflow openings rotationally symmetrically about the long axis of the probe, like a threaded section of a screw with several (in particular two or three) turns. Accordingly, the electrode devices are likewise so constructed as to be rotationally symmetrical with respect to the probe long axis.

A preferred embodiment of the invention will now be explained in greater detail with reference to the attached drawings.

DETAILED DESCRIPTION OF THE INVENTION

Figure 1:
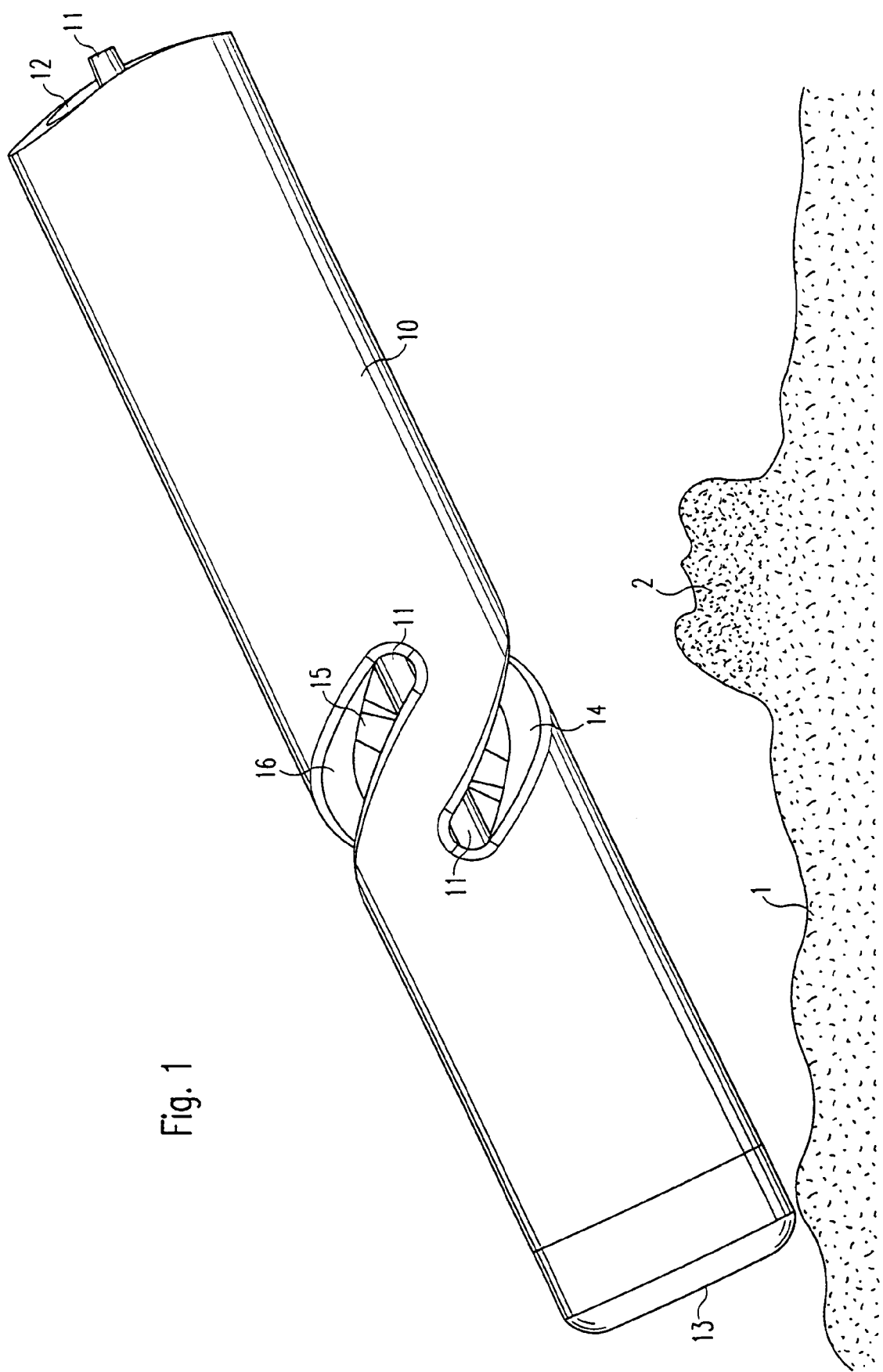
FIG. 1 shows an embodiment of the instrument schematically in perspective.
Figure 2:
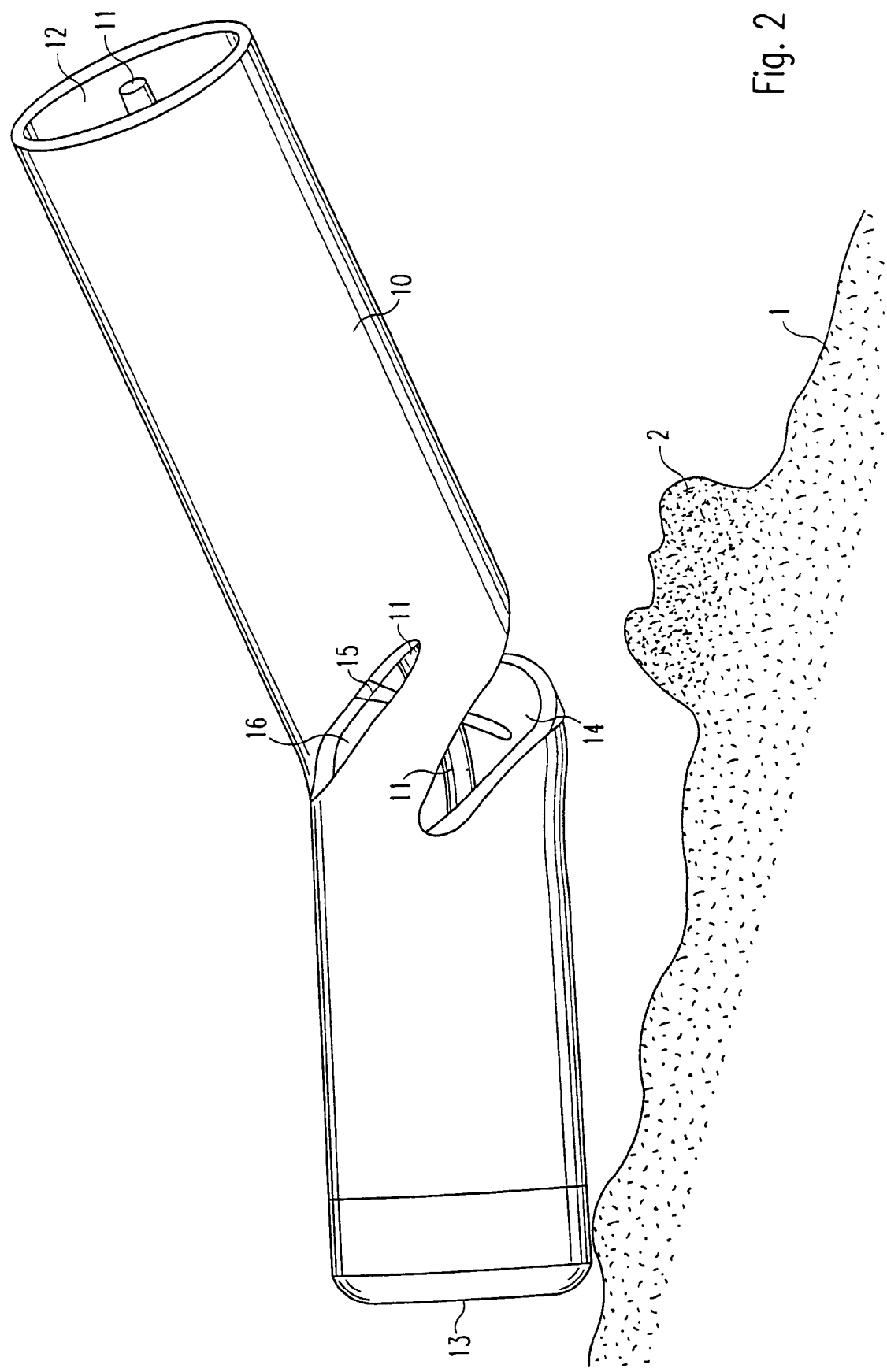
FIG. 2 shows the instrument according to FIG. 1 in the "bent" state.

In FIGS. 1 and 2 the reference numeral 10 designates an instrument in the form of a pipe or tube, in particular a probe, in particular made of Teflon, the end 13 of which is closed. Within it an electrode device, in particular a wire 11, is so disposed as to be approximately concentric with the long axis of the probe.

In the end region of the instrument 10 are disposed outflow openings 14, 15 and 16, uniformly spaced apart around the circumferential surface of the instrument 10 to form a screw-like pattern. During operation, when a noble gas, in particular argon or helium, is conducted through a lumen 12 of the instrument 10 while the instrument is in the state shown in FIG. 1, the gas flows uniformly through the outflow openings 14, 15 and 16, so that the end region of the instrument 10 is surrounded by a symmetrical "argon cloud". Now if a lesion 2 on the surface of a tissue 1 is to be coagulated, the instrument is brought into the vicinity of the lesion 2 as shown in FIG. 1. Whenever there is a danger that the plasma will be ignited not only towards lesion 2 but also towards other places in the tissue 1, in particular those opposite the lesion 2 (as can be the case in confined body cavities, such as in the bronchial system), then the instrument—as shown in FIG. 2—is positioned so that its end is pressed against the tissue 1. If the instrument 10 is made of appropriately flexible material, in particular in its end region (the preceding sections, connected to the gas source, can be made stiffer), the instrument then bends, causing the outflow openings identified as 15 and 16 in FIG. 2 to have a narrower cross section whereas the outflow opening 14, closest to the lesion 2, is expanded. As a result the flow of gas is controlled automatically so as to enable a targeted coagulation of lesion 2, with a preferential concentration of plasma between the electrode 11 and the lesion 2. The outflow openings 14, 15 and 16 can be dimensioned such as to permit not merely a constriction of certain outflow openings (15, 16) and an expansion of the other (14), but a complete closure on one side (14, 15) and opening of the otherwise closed outflow opening (16) on the other side. In this case the outflow openings 14, 15 and 16 are "cuts", the surfaces of which are apposed to one another when this section of the probe is in the un-bent state.

This arrangement is particularly advantageously implemented when the outflow openings 14, 15 and 16 are absolutely symmetrically disposed in the instrument, in particular are spaced at 120° intervals in the circumferential direction. The length of the slits in this case is made such that their ends are very close to one another (in terms of their angular circumferential position) or even overlap. This measure makes it impossible for an argon-free zone to be produced in the circumferential direction around the instrument 10.

LIST OF REFERENCE NUMERALS

1 Tissue
2 Lesion
10 Instrument
11 Electrode
12 Lumen
13 Closed end
14 First outflow opening
15 Second outflow opening
16 Third outflow opening

The invention claimed is:

1. An electrosurgical instrument for the coagulation of biological tissue comprising:
   a tubular probe for passing a noble gas from a gas source to at least two outflow openings defined in a distal end region of the probe, the at least two outflow openings each having a slit-like structure; and
   an electrode device disposed in the distal end region of the probe for being connected to an HF source for ionizing said noble gas in order to supply a coagulation current via said noble gas to said biological tissue;
   the at least two outflow openings being provided, disposed opposite one another with their long axes oriented perpendicular to or at an angle to, but not parallel to a long axis of the probe, and the probe being flexibly constructed at least in the region of the outflow openings, in such a way that when the probe is bent in the region of the outflow opening, their cross sections are enlarged or reduced.

2. The electrosurgical instrument as claimed in claim 1, wherein the outflow openings are constructed so as to extend around the probe in a helical configuration, resembling a screw threading with multiple turns.

3. The electrosurgical instrument as claimed in claim 1, wherein the outflow openings are uniformly spaced apart from one another, as viewed in the circumferential direction of the probe.

4. The electrosurgical instrument as claimed in claim 1, wherein all of the slit-like outflow openings have the same length.

5. The electrosurgical instrument as claimed in claim 1, wherein the ends of the outflow openings are equidistant from the end of the probe.

6. The electrosurgical instrument as claimed in claim 1, wherein the outflow openings are so constructed that the noble gas emerges in a planiform or fan-shaped stream.

7. The electrosurgical instrument as claimed in claim 1, wherein the electrode device is disposed in the interior of the probe and is disposed next to the outflow openings in such a way that the outflow openings are all at equal distances from the electrode device.

8. An electrosurgical instrument for the coagulation of biological tissue comprising:
   a noble gas source connection;
   a tubular probe operatively coupled to the noble gas source connection through which the noble gas can be passed to at least two outflow openings defined in a distal end region of the tubular probe, the at least two outflow opening each having a slit-like structure; and
   an electrode device disposed in the distal end region of the tubular probe, wherein the electrode device can be connected to a power source to supply a coagulation current,
   wherein the at least two outflow openings are disposed opposite one another with their long axes oriented perpendicular to or at an angle to, but not parallel to, a long axis of the tubular probe.

9. The electrosurgical instrument of claim 8, wherein the probe is flexibly constructed at least in the region of the outflow openings, in such a way that the cross section of the outflow openings changes when the probe is bent in the region proximate the outflow openings.

10. The electrosurgical instrument of claim 8, wherein the outflow openings are constructed so as to extend around the tubular probe in a helical configuration.

11. The electrosurgical instrument of claim 8, wherein the outflow openings are uniformly spaced apart from one another, as viewed in the circumferential direction of the tubular probe.

12. The electrosurgical instrument of claim 8, wherein the outflow openings have the same length.

13. The electrosurgical instrument of claim 8, wherein the ends of the outflow openings are equidistant from the distal end of the tubular probe.

14. The electrosurgical instrument of claim 8, wherein the outflow openings are constructed to allow the noble gas to emerge in one of a planiform stream and a fan-shaped stream.

15. The electrosurgical instrument of claim 8, wherein the outflow openings are disposed equidistant from the electrode device.

16. A method of performing a surgical procedure, comprising:

placing a tubular probe having at least two outflow openings disposed in a distal region of the tubular probe and an electrode device disposed in the distal region of the tubular probe in a region proximate a target of the surgical procedure;

providing a noble gas through the tubular probe so that the noble gas exits the tubular probe through the outflow openings;

providing an electrical current to the electrode device sufficient to ionize the noble gas; and bending the tubular probe in a region proximate the outflow openings thereby changing the cross section of the outflow openings.

17. The method of claim 16, further including directionally discharging the noble gas through the outflow openings.

18. The method of claim 16, wherein placing the tubular probe includes keeping the region surrounding the outflow openings substantially straight so that providing the noble gas through the tubular probe generates a symmetrical noble gas cloud around the tubular probe.

19. The method of claim 16, further including connecting the tubular probe to a noble gas source prior to providing the noble gas through the tubular probe.

* * * * *